United States Patent

Sakai et al.

[11] Patent Number: 5,804,518
[45] Date of Patent: Sep. 8, 1998

[54] ABSORBENT ARTICLES

[75] Inventors: Yoshihiro Sakai, Utsunomiya; Katsushi Maeda, Haga-gun; Yoshiaki Kumamoto, Kawachi-gun; Shingo Odajima, Haga-gun, all of Japan

[73] Assignee: Kao Corporation, Tokyo, Japan

[21] Appl. No.: 545,693

[22] PCT Filed: Mar. 20, 1995

[86] PCT No.: PCT/JP95/00510

§ 371 Date: Nov. 6, 1995

§ 102(e) Date: Nov. 6, 1995

[87] PCT Pub. No.: WO95/26208

PCT Pub. Date: Oct. 5, 1995

[30] Foreign Application Priority Data

Mar. 25, 1994 [JP] Japan .................................. 6-056326

[51] Int. Cl.$^6$ ................................ A61F 13/15; B32B 3/26
[52] U.S. Cl. .................... 442/370; 428/315.9; 442/373; 442/398; 604/369; 604/372; 604/378
[58] Field of Search ...................... 428/315.9; 604/378, 604/369, 372; 442/370, 373, 398

[56] References Cited

U.S. PATENT DOCUMENTS

| | | | |
|---|---|---|---|
| 4,206,980 | 6/1980 | Krueger | 350/359 |
| 4,539,256 | 9/1985 | Shipman | 428/315.5 |
| 4,609,584 | 9/1986 | Cutler et al. | 428/156 |
| 4,726,989 | 2/1988 | Mrozinski | 428/315.5 |
| 4,813,950 | 3/1989 | Branch | 604/396 |
| 4,820,293 | 4/1989 | Kamme | 604/368 |
| 5,043,209 | 8/1991 | Boisse et al. | 428/233 |
| 5,085,654 | 2/1992 | Buell | 604/370 |
| 5,106,383 | 4/1992 | Mulder et al. | 604/389 |
| 5,151,091 | 9/1992 | Glaug et al. | 604/385.1 |
| 5,169,712 | 12/1992 | Taff | 428/315.5 |
| 5,246,432 | 9/1993 | Suzuki et al. | 604/385.2 |
| 5,260,360 | 11/1993 | Mrozinski et al. | 524/95 |

FOREIGN PATENT DOCUMENTS 1044503  10/1966  United Kingdom.
1078895   8/1967  United Kingdom.

*Primary Examiner*—James J. Bell
*Assistant Examiner*—Blaine R. Copenheaver
*Attorney, Agent, or Firm*—Birch, Stewart, Kolasch & Birch, LLP

[57] ABSTRACT

An absorbent article having, as a back sheet, a porous sheet obtainable by preparing, by melt blending, a melt blended solution comprising 30 to 90 parts by weight of a crystalline polyolefin and 10 to 70 parts by weight of a compound with which the crystalline polyolefin is miscible and in which the crystalline polyolefin will dissolve at or above the melting point of the crystalline polyolefin but which will phase separate below the melting point of the crystalline polyolefin, molding the blended solution into a sheet, and stretching the sheet in at least one direction. The crystalline polyolefin is a polypropylene having a weight average molecular weight (Mw) to number average molecular weight (Mn) ratio (Mw/Mn) of no more than 6.0.

4 Claims, 1 Drawing Sheet

ABSORBENT ARTICLES

TECHNICAL FIELD

This invention relates to an absorbent article. More particularly, it relates to an absorbent article comprising a porous sheet which exhibits excellent tensile strength and high molding productivity as well as excellent moisture permeability and resistance to water pressure.

BACKGROUND ART

Porous sheets for absorbent articles have conventionally been produced by a process comprising molding a molten mixture of a polyolefin, such as polyethylene or polypropylene, and 40% by weight or more of an inorganic filler into a sheet and monoaxially or biaxially stretching the resulting sheet.

Porous sheets obtained by the above process are excellent in air- and moisture-permeability and cause no moisture condensation and are therefore useful as wall paper and wrapping paper. Addition of softness to these excellent properties makes the porous sheet suitable for use as an element of absorbent articles such as a back sheet of disposable diapers. In order to obtain soft porous sheets, it has been proposed to use linear low-density polyethylene as a polyolefin.

However, the conventional porous sheet has the following disadvantages for use as an element of absorbent articles such as disposal diapers.

For example, commonly employed disposal diapers are fabricated from an absorbent-member for absorbing excreta such as urine, a topsheet which covers the surface of the absorbent member and is directly applied to the skin, and a back sheet which covers the back side of the absorbent member and prevents leakage, these three parts being adhered together into a unitary body. The top and bottom ends and side edges of the diaper corresponding to the waist portion and a crotch portion are made stretchable for tight-fit to prevent leakage. The disposable diapers also have a fastening means such as tapes, with which the diaper is fitted to a wearer's body in use. The above-mentioned porous sheet is used as the back sheet.

The above-mentioned tapes provided for fastening (so-called fastening tapes) mostly have a width of about 25 to 35 mm for convenience of handling. However, when the fastening tape is unfastened to adjust the position of the diaper for a better fit or to see if urine has been discharged or not, the tape cannot be peeled without tearing the soft back sheet due to lack of strength. This being the case, the diaper must be changed with a new one. In order to avoid this, it has been proposed to provide wide tapes having a release surface (so-called landing tapes or target tapes) on the front side back sheet, on which fastening tapes may be removably adhered.

However, many problems are posed by the use of landing tapes. That is, the kinds of diaper constituting members and processes of production of diapers increase. A landing tape is more costly than any other diaper constituting members, so that use of the landing tape with a sufficient width increases the cost. In addition, even with a wide landing tape, cases are sometimes met with depending on the body size of a wearer, in which a fastening tape is adhered to the back sheet outside the landing tape area and cannot be stripped off.

Japanese Patent Application Laid-open 5-98057 discloses a high strength porous sheet obtained by blow molding a composition comprising a specific polyolefin, a filler, a specific plasticizer and a radical generator, and monoaxially stretching the blown film in the machine direction.

Although the sheet disclosed has nearly twice as much strength as a porous sheet obtained by a conventional process (a molten mixture of a polyolefin and an inorganic filler is molded into a sheet followed by stretching), such a degree of improvement is still insufficient for eliminating the necessity of landing tapes. In addition, since the use of the radical generator makes melt flow properties of the molded resin composition different from those of the composition before molding, it is difficult to recycle inevitably produced in the course of the production, resulting in reduced productivity.

Further, Japanese Patent Application Laid-open 5-38011 (corresponding to U.S. Pat. No. 4,539,256) discloses a microporous sheet obtained by a process comprising melt-blending a specific crystallizable polymer and a specific compound miscible with that polymer, molding the mixture into a sheet, causing phase separation to occur during a cooling step, and stretching the resulting sheeting.

Although the microporous sheet disclosed has two or three times as high strength as a sheet obtained by the conventional process (a molten mixture of a polyolefin and an inorganic filler is molded into a sheet followed by stretching), the strength still does not reach a sufficient level for making landing tapes needless. According to the present inventors' study, a porous sheet withstanding removal of a fastening tape therefrom is required to have at least 4 times, preferably 5 times, as high strength as a porous sheet obtained by the conventional process.

Besides, compared with the above-described conventional process for producing a porous sheet, the process for producing a microporous sheet as disclosed in the above patent involves problems that scattering of the compound miscible with the crystallizable polymer causes pollution of the working environment, and that wear of a screw and scorching of the polymer are likely to occur, so that the molding should be suspended occasionally for the molding machine to be taken apart and cleaned, resulting in poor industrial productivity.

DISCLOSURE OF THE INVENTION

An object of the present invention is to provide an absorbent article such as a disposable diaper comprising a porous sheet as a back sheet, in which the porous sheet exhibits markedly excellent tensile strength as well as moisture permeability and resistance to water pressure and can be produced at high productivity so that the diaper is inexpensive and easy to use. That is, the diaper can be fastened by adhering a fastening tape to any position of the back sheet regardless of the body size of a wearer with no need of providing a landing tape.

As a result of extensive investigations, the present inventors have found that the above object is accomplished by using a porous sheet made of specific polypropylene as a back sheet of an absorbent article. The present invention has been reached based on this finding.

The present invention provides an absorbent article comprising a liquid permeable topsheet, a liquid impermeable back sheet and an absorbent member interposed between said topsheet and said back sheet, said absorbent article being characterized in that:

said back sheet comprises a porous sheet obtainable by preparing, by melt blending, a melt blended solution comprising 30 to 90 parts by weight of a crystalline polyolefin and 10 to 70 parts by weight of a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction; and said crystalline polyolefin is a polypropylene having a weight average molecular weight (Mw) to number average molecular weight (Mn) ratio (Mw/Mn) of more than 6.0.

DETAILED DESCRIPTION OF THE INVENTION

Figure 1:
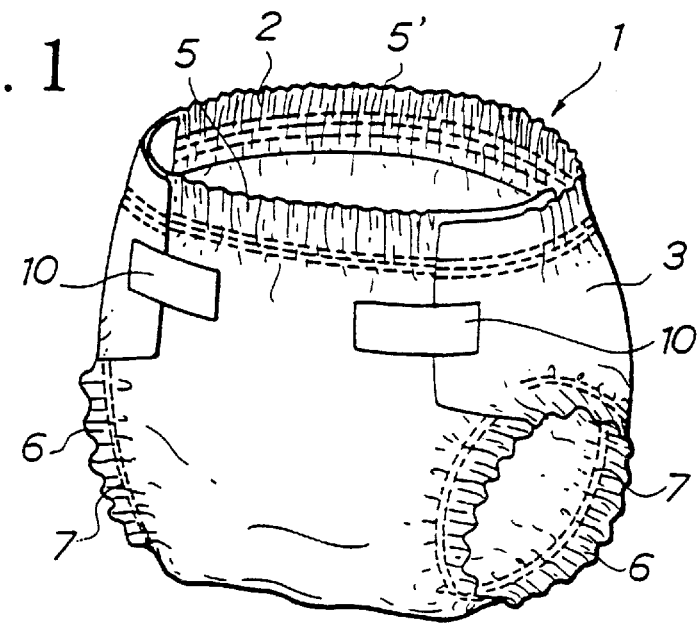
FIG. 1 is a perspective view of a disposable diaper as one embodiment of the absorbent article of the present invention.

The absorbent article according to the present invention will be described below in detail.

The absorbent article of the present invention is characterized by having the above-described porous sheet as a back sheet.

The crystalline polyolefin which is used in the porous sheet is polypropylene having a weight average molecular weight (Mw) to number average molecular weight (Mn) ratio (Mw/Mn) of more than 6.0, preferably more than 6.3.

An Mw/Mn ratio is a measure of molecular weight distribution. As long as the Mw/Mn ratio of the polypropylene is more than 6.0, when the polypropylene is melt-blended with, for example, not less than 20% by weight of the above-mentioned compound such as mineral oil, the mineral oil rapidly dissolves in the polypropylene so that they can be mixed in a stable manner.

If it is 6.0 or smaller, which means a narrow molecular weight distribution of the polypropylene, the polypropylene exhibits unstable dissolving properties with respect to the aforesaid compound such as mineral oil. This being the case, it is difficult to mix the polypropylene and the mineral oil at a prescribed mixing ratio. Additionally, in using a twin-screw extruder, a vent-up phenomenon occurs, and mixing cannot be effected smoothly, failing to perform extrusion stably.

The polypropylene having the above-specified molecular weight distribution can easily be obtained by polymerizing propylene in multiple stages in the presence of a prescribed catalyst. In more detail, an organoaluminum compound or a reaction product of an organoaluminum compound and ethyl ether is reacted with titanium tetrachloride to obtain a solid reaction product, which is further reacted with ethyl ether and titanium tetrachloride to obtain a solid reaction product. The resulting solid reaction product is combined with an organoaluminum compound and an aromatic carboxylic acid ester (a) to prepare a catalyst system having an aromatic carboxylic acid ester (a) to solid reaction product (b) molar ratio (a/b) of 0.1 to 10.0. The above-described polypropylene can easily be obtained by a multi-stage polymerization process in the presence of the thus prepared catalyst system in such a manner, for example, that 35 to 65% by weight of the total polymer is produced in the first stage and the balance, 35 to 65% by weight, is produced in the second and following stages.

The polypropylene preferably has a weight average molecular weight between 300,000 and 600,000 and a melting point between 155° C. and 170° C.

The polypropylene may be any of a homopolymer, a block copolymer or a random copolymer, or a mixture of two or more thereof. As long as the effects of the present invention are not impaired, the polypropylene may be used in combination with other polymers such as polyethylene.

Beside to the above-mentioned Mw/Mn ratio, it is preferable that the polypropylene satisfies the relationship: $1.00 \geq P \geq 0.015 \log MI+0.955$, wherein P is an isotactic pendant content; and MI is a melt index.

The isotactic pendant content (P) is indicative of crystallinity of polypropylene.

With P and MI satisfying the relationship $1.00 \geq P \geq 0.015 \log MI+0.955$, the polypropylene exhibits high crystallinity and improved rigidity. If P is less than $0.015 \log MI+0.955$, the polypropylene has reduced rigidity so that the porous sheet may have to have a large thickness for assuring rigidity necessary as a back sheet, which leads to an increase in cost.

The MI of the polypropylene preferably ranges from 0.03 to 2.0 g/10 min.

If the MI is less than 0.03, the molten polymer needs increased power in granulation or molding because of its poor fluidity, which is not only uneconomical but hinders speeding up of production. If it exceeds 2.0, the molten resin has reduced tension. It follows that, for example, a tubular film of the polypropylene is hard to lift in blown film extrusion, and sheeting becomes unstable.

The polypropylene satisfying the above relationship can be prepared by, for example, the process disclosed in Japanese Patent Publication 64-5051, p. 7, col. 13, 1. 44 to p. 8, col. 15, 1. 9.

The compound which is used in the porous sheet is a compound with which said crystalline polyolefin is miscible and in which said crystalline polyolefin will dissolve at or above the melting point of said crystalline polyolefin but which will phase separate below the melting point of said crystalline polyolefin.

The compound is not particularly limited as long as it possesses the above-mentioned characteristics. Suitable examples include mineral oils such as liquid paraffin, synthetic lubricating oils, dioctyl phthalate, diethyl phthalate, triethylene glycol, dibutyl phthalate, and esters of phthalic acid, trimellitic acid, pyromellitic acid and/or an aliphatic polybasic carboxylic acid and an alkyl alcohol.

The porous sheet to be used in the present invention is a porous sheet obtainable by preparing, by melt blending, a melt blended solution comprising 30 to 90 parts by weight, preferably 60 to 80 parts by weight, of a crystalline polyolefin and 10 to 70 parts by weight, preferably 20 to 40 parts by weight, of the compound, molding the melt blended solution into a sheet, and stretching the sheet at least in one direction.

If the proportion of the crystalline polyolefin is less than 30 parts by weight, the stretched sheet obtained has poor fabricability due to shortage of the matrix resin and, when rolled, undergoes collapse of fine pores or bleeding of the compound, such as mineral oil. If it exceeds 90 parts by weight, fine pores affording moisture permeability cannot be formed by stretching.

The temperature suitable for melt blending is at or above the melting point of the crystalline polyolefin, preferably ranging from 180° to 250° C. Melt blending for preparing a melt blended solution can be carried out in a twin-screw extruder. Polypropylene pellets are fed into a hopper in an constant amount, while the compound is fed into the vent of the twin-screw extruder.

In carrying out sheeting, the melt blended solution is preferably once cooled to prepare pellets of the blend. The pellets are blow molded by extrusion through a circular die of a single-screw extruder, or the pellets is blow molded by extrusion through a circular die connected to the tip of a twin-screw extruder via a gear pump.

In the sheeting, the following additives may be added to the melt blended solution in the amounts described below, all based on the total melt blended solution, if desired.

a) 0.5% by weight or less of a nucleating agent which controls the crystal size of polypropylene, such as aluminum p-tert-butylbenzoate, 1,2,3,4-dibenzylidene sorbitol or 1,2, 3,4-di-(p-ethylbenzylidene) sorbitol;

b) 1% by weight or less of an inorganic filler for tear prevention, such as anhydrous silica or zeolite;

c) 20% by weight or less of an opacifying inorganic filler, such as titanium oxide, barium sulfate, calcium carbonate or talc; and d) 0.05% by weight or less of a colorant, such as Phthalocyanine Blue, Quinacridone Red, Dioxane Violet or Isoindolinone.

In using the nucleating agent, it is preferably added as a nucleating agent masterbatch. The nucleating agent masterbatch is a pelletized mixture prepared by mixing a nucleating agent and a resin, such as polypropylene or polyethylene, with a solvent.

Stretching of the sheet is preferably conducted at a stretching temperature of 10° to 80° C. to a stretching ratio of 1.2 to 3 either monoaxially or biaxially.

The micro pores formed on stretching preferably have a pore size of 0.05 to 1 μm. The porous sheet preferably has a density of 0.7 to 0.85 g/cm$^3$, a basis weight of 10 to 60 g/m$^2$, and a thickness of 20 to 70 μm.

The method for obtaining the porous sheet of the present invention will be illustrated by way of a specific example, molding method (1).

Molding Method (1)

The melt blended solution comprising polypropylene and the compound at a prescribed ratio and, if desired, various additives is extruded by a twin-screw extruder (diameter: 45 mm; L/D: 33.5) at 230° C. into strands, cooled in a water bath, and pelletized by an pelletizer to prepare compounded pellets. The polypropylene is fed into a hopper, while the compound is fed into the middle part of the extruder by means of a diaphragm pump.

The compounded pellets are fed into an air cooling type blown-film extrusion machine, extruded from a circular die having a diameter of 200 mm at 210° C., and cooled by air at 20° C. blown from an air ring while being taken up at a take-up speed of 6 m/min to obtain a blown tube having a blow-up ratio of 2, a flat width of about 630 mm, and a thickness of about 50 μm. When a nucleating agent is added, a nucleating agent masterbatch and polypropylene are previously dry blended at a prescribed ratio and fed into the blown-film extrusion machine.

The resulting sheet is monoaxially stretched in the machine direction at 50° C. at a stretching ratio of 1.5 by means of a roller stretcher and subjected to annealing at 120° C. to obtain a porous sheet. The resulting porous sheet has a thickness of about 40 μm.

The thus obtained porous sheet preferably has a moisture permeability of 0.5 to 4.0 g/100 cm$^2$·hr. The porous sheet preferably has a yield strength (the stress at the yield point in the stress-strain curve in a tensile measurement) of 90 to 180 kgf/cm$^2$ provided that the yield strength is measured in the direction (MD or CD) which exhibits lower yield strength.

Figure 2:
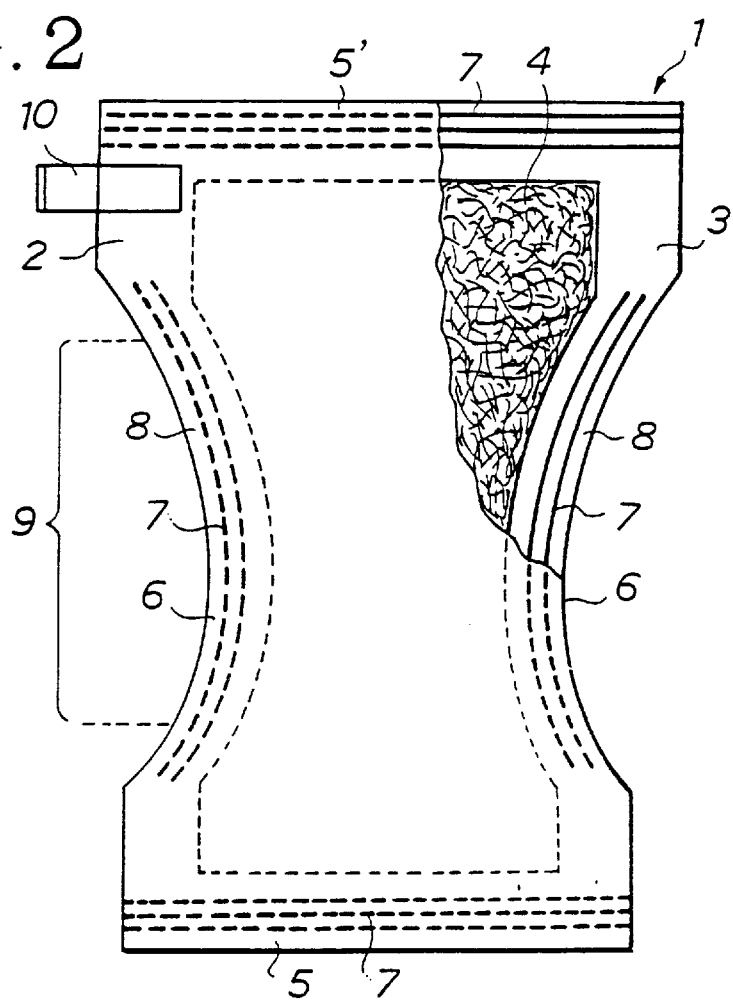
FIG. 2 is a perspective view of the disposable diaper shown in FIG. 1 in an unfolded condition and having a part thereof cut away.

The absorbent article according to the present invention will now be illustrated in greater detail by referring to FIGS. 1 and 2.

FIG. 1 is a perspective view of a disposable diaper as one embodiment of the absorbent article of the present invention. FIG. 2 is a perspective view of the disposable diaper shown in FIG. 1 in an unfolded condition and having a part thereof cut away.

The disposable diaper shown in FIGS. 1 and 2 comprises a liquid permeable topsheet 2, liquid impermeable back sheet 3 and an absorbent member 4 interposed between the topsheet 2 and the back sheet 3, in which back sheet 3 comprises the above-mentioned porous sheet.

In more detail, as shown in FIGS. 1 and 2, rear waist area 5', front waist area 5, crotch area 9, and side flaps 8 of the disposable diaper are fabricated from topsheet 2, back sheet 3, and absorbent member 4, each having an hourglass shape.

Elastic members 7 are provided between topsheet 2 and back sheet 3 in front waist area 5, rear waist area 5', and side flaps 8, respectively. A pair of tape fasteners 10 are provided on both edges of rear waist area 5', thereby enhancing the function and performance of the diaper.

As shown in FIG. 2, the disposable diaper is constituted such that it has longitudinal sides and that the topsheet 2 is almost the same as the back sheet in width and length.

The topsheet 2 is usually fabricated from nonwoven fabric having a basis weight of, for example, 15 to 40 g/m$^2$. As far as liquid permeable, a film, a net or the like may be used as the topsheet 2. The topsheet 2 with a hydrophilic central area and water-repellent peripheral area is particularly preferred.

The absorbent member 4 preferably comprises fluff (comminuted kraft pulp) covered with water-absorbing paper, preferably one containing superabsorbent polymer particles. The fluff usually weighs about 10 to 40 g. The superabsorbent polymer may be located in any of the upper, medium and lower layers of the absorbent member or be mixed with pulp. Examples of suitable superabsorbent polymers include starch types, cellulose types and synthetic polymer types, such as a starch-acrylic acid (or a salt thereof) graft copolymer, a saponified starch-acrylonitrile copolymer, cross-linked sodium carboxymethyl cellulose, and an acrylic acid (or a salt thereof) polymer. Such a superabsorbent polymer is capable of absorbing and retaining 20 times as much liquid as its own weight and gels on liquid absorption.

The elastic member 7 preferably comprises at least 1 and more preferably up to about 5 strings or ribbons of polyurethane, natural rubber, etc. or strings which become elastic on being wetted with water. The elastic member 7 has a length of about 30 to about 60% of that of a diaper and is preferably extensible about 1.3 to 2.0 times the original length.

While the absorbent article of the present invention has been explained by referring to flat type disposable diapers, the present invention is not limited thereto and is applicable to other articles, such as sanitary napkins, pads for incontinence, panty diapers, and the like.

The present invention will be described in greater detail with reference to Examples, but it should be understood that the present invention is not deemed to be limited thereto.

EXAMPLES 1 AND 2

A porous sheet was obtained by the above-described molding method (1) using 70 parts by weight of the polypropylene shown in Table 1, 25 parts by weight of the compound shown in Table 2, and 5 parts by weight of a nucleating agent masterbatch [nucleating agent("EC-1", a trade name produced by EC Kagaku K.K.; 2 wt. %)].

A disposable diaper shown in FIGS. 1 and 2 was fabricated using the resulting porous sheet as a back sheet.

EXAMPLE 3

A porous sheet was obtained by the above-described molding method (1) using 65 parts by weight of the polypropylene shown in Table 1 and 35 parts by weight of the compound shown in Table 2.

A disposable diaper shown in FIGS. 1 and 2 was fabricated using the resulting porous sheet as a back sheet.

EXAMPLES 4 TO 8

A porous sheet was obtained by the above-described molding method (1) using 70 parts by weight of the polypropylene shown in Table 1 and 30 parts by weight of the compound shown in Table 2.

A disposable diaper shown in FIGS. 1 and 2 was fabricated using the resulting porous sheet as a back sheet.

COMPARATIVE EXAMPLES 1 AND 2

A porous sheet was obtained by the above-described molding method (1) using 65 parts by weight of the polypropylene shown in Table 1, 30 parts by weight of the compound shown in Table 2, and 5 parts by weight of the same nucleating agent masterbatch as used in Example 1.

A disposable diaper shown in FIGS. 1 and 2 was fabricated using the resulting porous sheet as a back sheet.

The polypropylene used in Examples 1 to 8 and Comparative Examples 1 and 2 were tested in terms of items (1) to (3) described below, and the porous sheets obtained in these examples were tested in terms of items (4) to (9) described below. The results of tests (1) to (3) are shown in Table 1, and those of tests (4) to (9) are shown in Table 3.

(1) Melt Index (MI): Measured according to ASTM D1238 under a load of 2.16 kg.

(2) Isotactic Pendant Content (P): An isotactic content in the polypropylene molecular chain in terms of pendant content unit was obtained by 13C-NMR in accordance with Macromolecules, 8, 687 (1975).

(3) Mw/Mn: Determined from a weight average molecular weight (Mw) and a number average molecular weight (Mn) as measured by GPC (140° C., in o-dichlorobenzene solution).

(4) Moisture Permeability: Measured in accordance with JIS Z0208.

(5) Resistance to Water Pressure: Measured in accordance with JIS L1093B.

(6) Yield Strength: A yield strength of a 10 mm wide strip slit out of the sheet in the direction perpendicular to the stretching direction was measured with a Tensilon tensile tester at a pulling speed of 300 mm/min and a distance of 50 mm between chucks.

(7) Tear Strength: A 30 mm wide and 60 mm long test piece was cut out of the sheet in such a manner that the longitudinal sides of the piece were parallel to the stretching direction of the sheet, and a cut was made with a blade from the center of one shorter side by 30 mm along the longitudinal center line. Each of the two divided ends of the shorter side was fixed to each chuck to make the test piece a T-shape and torn apart along the stretching direction at a pulling speed of 300 mm/min. An average load obtained from the measurement chart was taken as a tear strength.

(8) Stability of Extrusion: The polypropylene and the compound was kneaded by feeding the compound into an open barrel in the middle of a twin-screw extruder. The stability of blending was evaluated according to the following standard.

E . . . Extrusion can be conducted in a stable manner free from vent-up of the extrudate, pulsation of the motor load or pulsation of the extrusion output.

F . . . Extrusion is possible while being accompanied by vent-up of the extrudate, pulsation of the motor load or pulsation of the extrusion output.

P . . . Extrusion is impossible due to noticeable vent-up of the extrudate, pulsation of the motor load or pulsation of the extrusion output.

(9) Strippability of Tape: A fastening tape was adhered to the porous sheet (back sheet) of the disposable diaper obtained in Examples and comparative Examples and then stripped off to evaluate the strippability according to the following standard.

The fastening tape used comprises a 80 μm thick polyethylene sheet having coated thereon Panel Master AM936 produced by Kanebo NSC Co., Ltd. by means of a bar coater and allowed to stand at room temperature for 24 hours to have a 30 μm thick adhesive layer and an adhesive area of 30×25 mm$^2$.

E . . . The fastening tape is strippable satisfactorily without causing a break or extension of the back sheet.

F . . . Stripping causes a slight tear of the back sheet.

P . . . Stripping causes a break of the back sheet.

TABLE 1

| | Polyolefin | | | | |
| --- | --- | --- | --- | --- | --- |
| | Manufacturer | Trade Name | MI(g/10 min) | P | Mw/Mn |
| Example 1 | Chisso Sekiyu Kagaku K.K. | WT6061 | 0.5 | 0.94 | 6.5 |
| Example 2 | Chisso Sekiyu Kagaku K.K. | WT6048 | 0.6 | 0.91 | 7.5 |
| Examples 3 to 8 | Chisso Sekiyu Kagaku K.K. | XF1932 | 0.4 | 0.91 | 6.5 |
| Comparative Example 1 | Showa Denko K.K. | FA122 | 2.4 | 0.94 | 4.0 |
| Comparative Example 2 | Idemitsu Petrochemical Co., Ltd. | F400S | 3.2 | 0.95 | 4.5 |

TABLE 2

|  | Compound | Manufacturer | Trade Name |
|---|---|---|---|
| Examples 1 to 3, Comparative Examples 1 and 2 | Liquid Paraffin | Idemitsu Petrochemical Co., Ltd. | PW90 |
| Example 4 | Synthetic Lubricating Oil | Idemitsu Petrochemical Co., Ltd. | HC600 |
| Example 5 | Dioctyl Phthalate | Kao Corp. | Vinysizer #80 |
| Example 6 | Diethyl Phthalate | — | — |
| Example 7 | Triethylene Glycol | — | — |
| Example 8 | Dibutyl Phthalate | — | — |

TABLE 3

Results of Evaluation

|  | Moisture Permeability (g/100 cm$^2$ · hr) | Resistance to Water Pressure (mAq) | Yield Strength (Kgf/cm$^2$) | Tear Strength (gf) | Stability of Extrusion | Tape Strippability |
|---|---|---|---|---|---|---|
| Example 1 | 2.1 | >2.0 | 104 | 21 | E | E |
| Example 2 | 1.9 | >2.0 | 147 | 23 | E | E |
| Example 3 | 2.5 | >2.0 | 101 | 16 | E | F |
| Example 4 | 2.2 | >2.0 | 130 | 17 | E | E |
| Example 5 | 2.3 | >2.0 | 128 | 19 | E | E |
| Example 6 | 1.9 | >2.0 | 128 | 18 | E | E |
| Example 7 | 1.9 | >2.0 | 125 | 19 | E | E |
| Example 8 | 2.0 | >2.0 | 129 | 17 | E | E |
| Compara. Example 1 | 1.9 | >2.0 | 82 | 13 | F | P |
| Compara. Example 2 | 2.1 | >2.0 | 79 | 11 | F | P |

INDUSTRIAL APPLICABILITY

The absorbent article according to the present invention comprises, as a back sheet, a porous sheet excellent in tensile strength, molding productivity as well as moisture permeability and water pressure resistance. Therefore, there is no need of providing a landing tape, and the absorbent article is inexpensive and is easy to use in that a fastening tape may be adhered to any position of the back sheet regardless of the body size of a wearer.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

We claim:

1. An absorbent article comprising a liquid permeable topsheet, a liquid impermeable back sheet and an absorbent member interposed between said topsheet and said back sheet, said absorbent article being characterized in that:

said back sheet being a single continuous porous sheet obtainable by preparing, by melt blending, a solution comprising 30 to 90 parts by weight of a crystalline polyolefin and 10 to 70 parts by weight of a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction;

said crystalline polyolefin being a polypropylene having a weight average molecular weight (Mw) to number average molecular weight (Mn) ratio (Mw/Mn) of more than 6.0.

2. The absorbent article as claimed in claim 1, wherein said polypropylene has an isotactic pendant content (P) and a melt index (MI) satisfying the relationship:

$$1.00 \geq P \geq 0.015 \log MI + 0.955$$

3. The absorbent article as claimed in claim 1, wherein said compound is at least one compound selected from the group consisting of a mineral oil, a synthetic lubricating oil, dioctyl phthalate, diethyl phthalate, triethylene glycol, dibutyl phthalate, and an ester of phthalic acid, trimellitic acid, pyromellitic acid and/or an aliphatic polybasic carboxylic acid and an alkyl alcohol.

4. The absorbent article as claimed in claim 1, wherein said porous sheet had a moisture permeability of 0.5 to 4.0 g/100 cm$^2$·hr.

* * * * *